United States Patent
Deheri et al.

(10) Patent No.: US 9,592,499 B2
(45) Date of Patent: Mar. 14, 2017

(54) PROCESS FOR THE ISOLATION OF CAROTENOIDS

(71) Applicant: ShayoNano Singapore Pte Ltd, Singapore (SG)

(72) Inventors: Pratap Kumar Deheri, Singapore (SG); Srinivasan Varadalambedu Nithianandam, Singapore (SG); Mahesh Dahyabhai Patel, Singapore (SG)

(73) Assignee: ShayoNano Singapore Pte Ltd, Singapore (SG)

( * ) Notice: Subject to any disclaimer, the term of this patent is extended or adjusted under 35 U.S.C. 154(b) by 144 days.

(21) Appl. No.: 14/398,835

(22) PCT Filed: Feb. 20, 2014

(86) PCT No.: PCT/SG2014/000072
§ 371 (c)(1),
(2) Date: Nov. 4, 2014

(87) PCT Pub. No.: WO2014/129974
PCT Pub. Date: Aug. 28, 2014

(65) Prior Publication Data
US 2015/0133712 A1    May 14, 2015

(30) Foreign Application Priority Data
Feb. 22, 2013    (GB) .................................. 1303175.2

(51) Int. Cl.
| | |
|---|---|
| B01J 39/02 | (2006.01) |
| A23L 5/44 | (2016.01) |
| A23L 33/105 | (2016.01) |
| B01J 20/06 | (2006.01) |
| C07C 403/24 | (2006.01) |
| C09B 61/00 | (2006.01) |
| B01J 20/10 | (2006.01) |
| B01J 39/14 | (2006.01) |
| C07C 7/00 | (2006.01) |
| C07C 7/10 | (2006.01) |
| C07C 7/12 | (2006.01) |
| B01J 20/08 | (2006.01) |
| B01J 20/12 | (2006.01) |
| B01J 20/18 | (2006.01) |
| B01J 20/02 | (2006.01) |

(52) U.S. Cl.
CPC ................. *B01J 39/02* (2013.01); *A23L 5/44* (2016.08); *A23L 33/105* (2016.08); *B01J 20/0233* (2013.01); *B01J 20/06* (2013.01); *B01J 20/08* (2013.01); *B01J 20/10* (2013.01); *B01J 20/103* (2013.01); *B01J 20/12* (2013.01); *B01J 20/18* (2013.01); *B01J 39/14* (2013.01); *C07C 7/005* (2013.01); *C07C 7/10* (2013.01); *C07C 7/12* (2013.01); *C07C 403/24* (2013.01); *C09B 61/00* (2013.01); *C07C 2101/16* (2013.01)

(58) Field of Classification Search
None
See application file for complete search history.

(56) References Cited

U.S. PATENT DOCUMENTS 4,443,379 A    4/1984    Taylor et al.

FOREIGN PATENT DOCUMENTS

| | | |
|---|---|---|
| GB | 2218989 A | 11/1989 |
| JP | 61-282357 A | 12/1986 |

OTHER PUBLICATIONS

International Search Report and Written Opinion for related PCT Application No. PCT/SG2014/000072, filed Feb. 20, 2014, Report dated Apr. 2, 2014, 7 pages.
NDE-AGA, J. et al., Adsorption of Palm Oil Carotene and Free Fatty Acids onto Acid Activated Cameroonian Clays, Journal of Applied Science, 2007, vol. 7, No. 17, pp. 2462-2467.
Beklemyshev, V. et. al., Nanostructured Biocides for Means of Rehabilitation, 2014, G Ital Med Lav Erg, 2010, vol. 32, No. 1, pp. 59-67.

*Primary Examiner* — Tam M Nguyen
(74) *Attorney, Agent, or Firm* — Hovey Williams LLP

(57) ABSTRACT

Described herein is a material for reversibly binding to a carotenoid comprising a support coupled to silver ions in an amount to enable reversible binding with carotenoids, and wherein with the exception of silver ions, is substantially free of transition metals. Also described herein is a process for reversibly binding a carotenoid, the process comprising the steps of: providing a support coupled to silver ions in an amount to enable reversible binding with the carotenoid, wherein with the exception of silver, the support is substantially free of transition metals, contacting the support with the carotenoid under binding conditions to bind it thereto and dissociating the carotenoidod from the support under dissociating conditions to release the carotenoid.

32 Claims, 5 Drawing Sheets

PROCESS FOR THE ISOLATION OF CAROTENOIDS

RELATED APPLICATIONS

This application is a national stage application, under 35 U.S.C. §371 of International Patent Application No. PCT/SG2014/000072, filed on Feb. 20, 2014 and published as WO 2014/129974 on Aug. 28, 2014, which claims priority to GB Patent Application No. 1303175.2, filed on Feb. 22, 2013, which is hereby incorporated by reference in its entirety.

TECHNICAL FIELD

The present disclosure generally relates material and process for isolating carotenoids.

BACKGROUND

Carotenoids are naturally occurring pigments that are responsible for many of the vivid yellow, orange, and red colors observed in living organisms. Carotenoids are widely distributed in nature and perform a number of important biological functions, such as serving as light harvesting pigments in photosynthesis and protecting organisms from photo-oxidative damage.

In humans, carotenoids provide powerful antioxidant action, protecting the body from free radicals, which can develop as a result of normal metabolism as well as from exposure to pollution and other environmental hazards. Carotenoids also find use as natural pigments in foods and cosmetic products and in the nutraceutical/pharmaceutical industries as dietary precursors of vitamin A.

The global market for carotenoids is projected to top $1.2 billion US dollars by 2015. At the present time, close to 90% of the carotenoids on the market are produced by chemical synthesis. However, there is a growing interest in the development of processes for isolating carotenoids from sources in nature. It is well known that certain plants contain large amounts of carotenoids.

Palm oil is one of the richest sources of natural plant carotenoids known. Depending on its origin, palm oil can have between 500 and 7,000 mg/kg of carotenoids.

A number of processes for recovering carotenoids from palm oil or concentrating carotenoids are known. These methods include chemical modification of the oil and distillation, liquid-liquid extraction, and chromatography.

In one known process, palm oil is transesterified and then concentrated by extraction and distillation. In this process, palm oil is first transesterified with an alcoholic solvent, such as methanol forming fatty acid esters and glycerol. Once the reaction mixture is allowed to separate, the upper phase consisting of fatty acid ester with dissolved carotenoid is washed with a mixture of alcohol and water and then with water alone. The complete or partial removal of the fatty acid ester by distillation leaves a carotenoid concentrate. The distillation step is carried out in vacuo at temperatures of up to 150° C., which can take about 5 hours. In this process, the palm oil must be converted into a non-edible ester to aid in separation of the constituents of the palm oil. Thus, the processed palm oil material cannot be used in the preparation of food products. In addition, carotenoids readily decompose at the distillation temperature, which decreases the isolated yield and purity of the carotenoids left in the carotenoid concentrate.

Supercritical $CO_2$ has also been used to isolate carotenoids from palm oil. In this process, palm oil is added to a high pressure extraction vessel and super critical carbon dioxide is passed through the vessel, extracting the carotenoids in the material in the process. The extract is collected and the carbon dioxide is then allowed to evaporate from the carotenoid extract. While this process produces carotenoid extracts in good purity, it is disadvantaged by the high cost of the process, the high operating pressures, and the very low solubility of carotenoids in super critical carbon dioxide.

In view of the foregoing limitations of existing isolation processes, there exists a need to develop an efficient and cost effective process for isolating carotenoids from liquids, such as palm oil, which does not modify the oil into non-edible compounds. In addition, there is also a need to develop a material for isolating carotenoids. The present disclosure addresses these needs and has related advantages.

SUMMARY

According to a first aspect, there is provided a material for reversibly binding to a carotenoid, the material comprising: a support coupled to silver ions in an amount to enable reversible binding with said carotenoid, and wherein, with the exception of silver ions, said support is substantially free of transition metals.

Advantageously, because the support is substantially free of transition metals, the extent of reversible binding occurring between the carotenoid and the support is greater compared to a support that contains transition metals under the same reaction conditions. In one embodiment, the support is synthetic clay that is substantially free of transition metals and which is coupled to or doped with silver ions.

In embodiments, the support has a larger surface area relative to natural clay, which leads to greater binding of the carotenoid to the support. The support may comprise a surface area of from about 400 $m^2/g$ to about 700 $m^2/g$. In embodiments, the surface area may be selected from the group consisting of: 400 $m^2/g$, 425 $m^2/g$, 450 $m^2/g$, 475 $m^2/g$, 500 $m^2/g$, 525 $m^2/g$, 550 $m^2/g$, 575 $m^2/g$, 600 $m^2/g$, 625 $m^2/g$, 650 $m^2/g$, 675 $m^2/g$ and 700 $m^2/g$.

According to a second aspect, there is provided a process for reversibly binding a carotenoid, the process comprising the steps of: providing a, support coupled to silver ions in an amount to enable reversible binding with said carotenoid, and wherein, with the exception of silver ions, said support is substantially free of transition metals; contacting the support with the carotenoid under binding conditions to bind it thereto; dissociating the carotenoid under dissociation conditions to release said carotenoid.

Advantageously, it has been found that a support which has been coupled with silver ions is able to achieve reversible binding with carotenoids. Advantageously, the reversible binding of the carotenoids to the silver ions-doped support is such that the carotenoid can be readily extracted in an appropriate organic solvent, without the need for harsh extraction conditions, e.g., high temperatures. Advantageously, the extraction conditions do not denature the carotenoids.

Also disclosed herein is a process comprising the steps of contacting a liquid containing at least one carotenoid with a composition comprising at least one pi-bond-philic species thereby forming a mixture comprising a carotenoid complex and the liquid; and removing the carotenoid complex from the liquid.

The process can further comprise the steps of contacting the carotenoid complex with a wash solvent thereby forming a washed carotenoid complex; and extracting the carotenoid from the washed carotenoid complex with an organic solvent to form an extract phase containing at least one carotenoid. The process can further comprise the step of removing the organic solvent from the extract phase containing at least one carotenoid by evaporation, thereby forming a concentrated carotenoid extract.

Advantageously, the process can be used to isolate carotenoids from liquids containing carotenoids, such as palm oil, in a highly efficient and selective manner. As little as 2% by weight of the composition (relative to the weight of the liquid) can be used to effectively isolate a large portion of the carotenoids present in the liquid.

Furthermore, compounds such as tocopherol, tocotrinol, and cholesterol that can be present in the liquid containing at least one carotenoid can be effectively separated from the recovered carotenoids during the isolation process described herein. Thus, the carotenoids isolated using the process described herein can be substantially free of such compounds. A further advantage of the process described herein is that when palm oil is processed, the recovered palm oil is unmodified by the isolation process and thus can be used in food products and other applications that utilize the glycerol esters found in palm oil.

According to a third aspect, there is provided a synthetic hectorite clay, wherein at least some of the sodium ions present in the hectorite clay have been exchanged with silver ions. In one embodiment, at least 70 mol % to 100 mol % of the sodium ions present in the hectorite clay have been exchanged with silver ions.

In one embodiment, the synthetic, silver ions-doped, hectorite clay is used as a support in the above disclosed processes. In embodiments, the mol % of the sodium ions that have been exchanged with silver ions may be selected from the group consisting of: 70 mol %, 75 mol %, 80 mol %, 85 mol %, 90 mol %, 95 mol % and 100 mol %.

The material according to the first aspect can be readily prepared from commercially available and inexpensive starting materials. The material can also be reused, which leads to further reductions in processing costs.

DEFINITIONS

The following words and terms used herein shall have the meaning indicated:

As used in the context of the present specification, the terms "bind" or "binding" refer to the attractive interaction of two entities that have affinity for each other and which includes the formation of a covalent or a non-covalent bond between the two entities.

The term "reversible binding" is defined as the ability of two entities to bind and dissociate reversibly under suitable reaction conditions, wherein the chemical structures of either or both entities are not substantially altered before and after binding.

The term "coupled" and "coupling" as used herein refer to any chemical association and includes both covalent and non-covalent interactions.

As used herein, the terms "cation exchange capacity" and "cation exchanging capacity" of a cation exchanging layered material (e.g., a natural or synthetic clay) are synonymous and represent an amount of a set of exchangeable cations and describes a capability to replace one set of exchangeable cations (typically a capability to replace, if desired, native inorganic ions such as sodium cation, lithium cation, calcium cation and/or hydrogen cation) with another set of cations, e.g., a pi-bond-philic species. The "exchangeable cations" can be monovalent cations, polyvalent cations, or a mixture thereof, each cation having a formal positive charge.

As used herein, "intercalated" means a layered material in which atoms, ions, molecules, polyatomic ions, or other substances have been absorbed between layers of such materials and/or have complexed and/or exchanged with the exchangeable cations on surfaces of such layers.

The term "carotenoid" is understood in the art to refer to a structurally diverse class of polyene pigments derived from isoprenoid pathway intermediates and synthetic/semi-synthetic analogs thereof. Carotenoids can be divided into two broad classes, (1) xanthophylls (which contain oxygen) and (2) carotenes (which are hydrocarbons that contain no oxygen). Exemplary carotenoids include α-carotene and β-carotene.

The term "pi-bond-philic species" refers to a metal, metalloid, metal ion, metalloid ion, or other ion that is capable of binding with the pi system of a carbon carbon double bond (either by interaction with the π bonding orbital, the π anti-bonding orbital or both). Exemplary pi-bond-philic species include, but are not limited to metals, metalloids, metal ions, and metalloid ions that are capable of binding with the pi system of a carbon carbon double bond selected from the group consisting of Group II, Group III, Group IV, Group V, Group VI, Group VII, Group VIII. Additional exemplary pi-bond-philic species include, but are not limited to metals and metal ions that are capable of binding with the pi system of a carbon carbon double bond selected from the group consisting of lanthanoid and actinoid elements. In instances where the pi-bond-philic species is a metal ion (cation or anion) the pi-bond-philic species can include the metal ion and its associated counter ions (e.g., boron tetrafluoride, carbonate, halide, hydroxide, nitrate, oxide, super oxide, acetate, alkoxide, cyanide, phosphate, sulfate, and the like). An exemplary pi-bond-philic species for use in the disclosed material and process is a silver species, including silver ions, and silver-containing compounds. The silver ions or the silver stoichiometry in the silver-containing compounds can be monovalent, divalent or trivalent.

As used herein, the term silicate or silicates refers to an anionic silicon containing ion, such as $[SiO_4]^{4-}$, $[Si_2O_7]^{6-}$, $[Si_nO_{3n}]^{2n-}$, $[Si_{4n}O_{11n}]^{6n-}$, $[Si_{2n}O_5]^{2n-}$, and $[Al_xSi_yO_{2(x+y)}]^{x-}$, and combinations thereof, wherein n, x, and y are independently selected from 1-100. In certain embodiments, silicates refers to $[SiO_4]^{4-}$, $[Si_2O_7]^{6-}$, and combinations thereof.

The term "synthetic clay" is to be interpreted broadly to include materials related in structure to layered clays and porous fibrous clays such as synthetic hectorite (lithium magnesium sodium silicate). It will be appreciated that within the scope of this disclosure the following classes of clays have application alone or in combination and in mixed layer clays: kaolinites, serpentines, pyrophyllites, talc, micas and brittle micas, chlorites, smectites and vermiculites, palygorskites, sepiolites, allophane and imogolite. The following references describe the characterization of clays of the above types: *Chemistry of Clay and Clay Minerals*. Edited by A. C. D. Newman. Mineralogical Society Monograph No. 6, 1987, Chapter 1; S. W. Bailey; *Summary of recommendations of AIPEA Nomenclature Committee*, Clay Minerals 15, 85-93; and *A Handbook of Determinative Methods in Mineralogy*, 1987, Chapter 1 by P. L. Hall.

The word "substantially free" refers to an amount of a substance that is sufficiently low such that the substance contributes no significant properties to the bulk and, in any event, will be less than 5% by weight and preferably less than 1% by weight. The term "substantially free" does not exclude completely free. In the context of the present specification, the term "substantially free" when used to refer to an amount of transition metals in the support material, denotes an amount of transition metal less than 5% by weight, preferably less than 3% by weight, even more preferably less than 1% by weight, and further includes a situation where transition metals (apart from silver) are completely absent.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

DISCLOSURE OF OPTIONAL EMBODIMENTS

Provided herein is a process for the isolation of carotenoids from a liquid containing carotenoids. Suitable liquids include, but are not limited to palm oil, crude palm oil, crude palm olein, red palm oil/olein, palm stearin, neutralized red palm oil, neutralized red palm olein, sunflower oil, coconut oil, wheat germ oil, carrot oil, soybean oil, rapeseed oil, olive oil and derivatives of such oils.

In one embodiment, the disclosed process comprises the steps of: providing a support coupled to silver ions in an amount to enable reversible binding with the carotenoid, and wherein, with the exception of silver ions, said support is substantially free of transition metals; contacting the support with the carotenoid under binding conditions to bind it thereto; dissociating the carotenoid from the support under dissociation conditions to release the carotenoid.

The support may be selected to have a higher surface area relative to natural clay. The support may be selected to have a surface area of from 400 m²/g to 700 m²/g.

In one embodiment, the support selected for use in the above disclosed process is synthetic clay. Advantageously, the synthetic clay may be substantially homogeneous in its chemical composition. The synthetic clay may also advantageously exhibit greater surface area for binding carotenoids thereto, relative to non-synthetic clay support materials.

The process may further comprise a step of, prior to the contacting step, a step of partially or completely exchanging indigenous cations of the support with silver ions.

In one embodiment, the support is selected to have the following formula:

$$Na_{1.2-(X \cdot Y)}(Ag^{(Y)})_X[Mg_{4.8}Li_{1.2}Si_8O_{20}(OH)_4],$$

wherein X is a number selected from 0.01-1.2;
Y is a whole number selected from 1-3; and
wherein the material has a net neutral charge.

In one embodiment, the support is selected such that the product of X and Y is 1.2. That is, substantially all the sodium ions formerly present in the support may be exchanged or replaced by silver ions.

The process may further comprise the steps of contacting the carotenoid with a wash solvent to form a washed carotenoid; contacting the washed carotenoid with an organic solvent to form an extract phase containing carotenoids.

The liquid containing carotenoids can be an extract derived from carotenoid producing fungi, carotenoid producing bacteria, carotenoid producing microalgae, and carotenoid producing yeast. In one embodiment, the carotenoid is provided in a liquid selected from a fruit oil, vegetable oil, or an extract derived from the group selected from carotenoid producing fungi, carotenoid producing bacteria, carotenoid producing microalgae, and carotenoid producing yeast. In a preferred embodiment, the liquid is palm oil. The solvent used for the extract can be an organic solvent, aqueous solvent, and combinations thereof. Suitable extraction solvents are well known to those of skill in the art and can include water, alcohols (e.g., methanol, ethanol, and i-propanol), ethers (e.g., diethyl ether, t-butylmethylether, tetrahydrofuran, 2-methyl-tetrahydrofuran, and pyran) esters (e.g., ethyl acetate and butyl acetate), ketones (e.g., acetone and 2-methyletyhl ketone), alkylhalides (e.g., dichloromethane, chloroform, and carbontetrachloride), aromatic hydrocabons (e.g., benzene, toluene, and xylenes), aliphatic hydrocarbons (e.g., pentanes, hexanes, and petroleum ether), and combinations thereof.

The isolation process can also be used in connection with the purification and/or isolation of synthetic carotenoids, such as β-carotene. Thus, the liquid containing carotenoids can be an organic solvent used in the chemical synthesis and/or purification of carotenoids. Suitable organic solvents include, but are not limited to alcohols, alkanes, aromatic compounds, ethers, esters, haloalkanes, ketones, and combinations thereof.

The process can be used to isolate carotenoids and related compounds. In certain instances, the process described herein can be used to isolate olefinic and polyolefinic carotenoids. Exemplary carotenoids include, but are not limited to antheraxanthin, adonirubin, adonixanthin, astaxanthin, canthaxanthin, capsorubrin, β-cryptoxanthin, α-carotene, β-carotene, β,ψ-carotene, δ-carotene, ε-carotene, echinenone, 3-hydroxyechinenone, 3'-hydroxyechinenone, γ-carotene, ψ-carotene, 4-keto-γ-carotene, ζ-carotene, α-cryptoxanthin, deoxyflexixanthin, diatoxanthin, 7,8-didehydroastaxanthin, didehydrolycopene, fucoxanthin, fucoxanthinol, isorenieratene, β-isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, torulene, 4-keto-torulene, 3-hydroxy-4-keto-torulene, uriolide, uriolide acetate, violaxanthin, zeaxanthin-β-diglucoside, and zeaxanthin.

The isolation process described herein provides concentrates comprising carotenoids. Such concentrates can range in concentration from 5% to 100% by weight of carotenoids.

If desired, the concentrate can be further purified by traditional purification techniques, such as chromatography, distillation, crystallization, liquid-liquid extraction, liquidsolid extraction, and filtration.

In the first step of the isolation process, the carotenoid can be brought into contact with a material comprising at least one pi-bond-philic species capable of binding a carotenoid. Carotenoids are a family of highly conjugated organic compounds. Thus, pi-bond-philic species that can reversibly bind with one or more of the olefins and optionally the other functional groups present in carotenoids can be used as pi-bond-philic species. Any metal, metal salt, or metal complex capable of binding an olefin or conjugated olefin can be used as a pi-bond-philic species. Suitable pi-bond-philic species include, but are not limited to Group II, Group III, Group IV, Group V, Group VI, and Group VII elements. Exemplary metals, metal salts, or metal complexes comprises a metal selected from the group consisting of Zn, Ca, Ni, Cu, Au, Pd, Pt, Fe, Ni, Rh, Ir, Hg, and Cd and combinations thereof. In certain embodiments, the pi-bond-philic species comprises a metal selected from the group consisting of Ag, Zn, Ca, Cu, and Au. Iodine in the neutral or +1 oxidation state can also be used as a pi-bond-philic species. The pi-bond-philic species can be present in any oxidation state. Suitable oxidation states include 0, +1, +2, +3, +4, +5 or +6. In one embodiment, it is preferred that the pi-bond-philic species is monovalent, divalent or trivalent silver ions.

In one embodiment, the support is doped with silver ions and the silver-doped support is present in an amount of about 1:100 to about 10:1 (wt:wt) relative to the amount of the liquid containing at least one carotenoid. In certain instances, the silver-doped support is present in an amount of about 1:100 to about 2:1; about 1:100 to about 1:1; about 1:100 to about 1:2; about 1:100 to about 1:4; about 1:100 to about 1:9; or about 1:100 to about 1:19 (wt:wt) relative to the liquid containing at least one carotenoid. In certain instances, the silver-doped support is present in less than about 30% by weight, less than about 25% by weight, less than about 20% by weight, less than about 15% by weight, less than about 10% by weight, less than about 5% by weight, less than about 3% by weight, less than about 2% by weight, less than about 1% by weight relative to the amount of the liquid containing at least one carotenoid. In embodiments, the ratio of the silver-doped support to the liquid by weight may be selected from the group consisting of: 0.01:1, 0.02:1, 0.05:1, 0.06:1, 0.07:1, 0.08:1, 0.09:1 and 0.1:1. In a preferred embodiment, the silver-doped support is present in an amount of about 0.01:1 to about 0.1:1 by weight relative to the liquid.

The amount of time that the liquid containing at least one carotenoid and the silver-doped support remain in contact can be from about 5 minutes to about 12 hours. In certain instances, the liquid containing at least one carotenoid and the silver-doped support are contacted for a duration selected from the group consisting of: about 10 minutes, about 30 minutes, about 1 hour, about 2 hours, about 3 hours, about 4 hours, about 5 hours, about 6 hours, about 7 hours, about 8 hours, about 9 hours, about 10 hours, about 11 hours and about 12 hours. In one embodiment, it is preferred that the time for contacting the carotenoid with the silver-doped support is from about 10 minutes to about 6 hours.

In certain instances, the liquid containing at least one carotenoid is passed over or through the silver-doped support in a continuous process.

The liquid containing at least one carotenoid and the silver-doped support can be mixed, e.g., agitated or stirred, or allowed to sit, and combinations thereof during the contact time. Possible agitation elements include traditional stirrers, rotating magnetic rods, bladder devices integral with the structure of the container, as well as different devices for manipulating the shape of the mixing container.

Upon reversible binding of the support to the carotenoid, excess liquid can optionally be removed by evaporation, centrifugation, filtration, decanting; and/or by washing with a wash solvent.

The liquid can be separated from the carotenoid by first centrifuging the mixture, which causes the carotenoid to settle to the bottom of the vessel, and then the excess liquid can be decanted. Small amounts of the liquid may remain in the bound carotenoid.

The liquid can be removed from the carotenoid by filtration. Filtration refers to a process of separating particulate matter from a liquid, by passing the liquid carrier through a medium that will not pass at least some or substantially all of the particulates. Filtration can be accomplished by using gravity or by the application of pressure or vacuum to force the liquid through the filter medium.

In embodiments, the bound carotenoid (that is reversibly coupled to the support) is contacted with a wash solvent to form a washed carotenoid. The wash solvent can be any organic solvent that is at least partially miscible with, the liquid containing at least one carotenoid and does not displace the bound carotenoids from the support to an appreciable extent.

Suitable wash solvents include, but are not limited to alcohols, alkanes, aromatics, ethers, esters, ketones, alkyl halides, and combinations thereof. Exemplary wash solvents include, but are not limited to methanol, ethanol, n-propanol, iso-propanol, n-butanol, iso-butanol, tert-butanol, acetone, methyl ethyl ketone, diethyl ether, tert-butyl methyl ether, tetrahydrofuran, 2-methyl tetrahydrofuran, lower alkanes, such as pentanes, hexanes, and octanes, petroleum ether, ethyl acetate, butyl acetate, benzene, toluene, dichloromethane, dichloroethane, chloroform, and carbon tetrachloride. In certain instances, the wash solvent is a food grade solvent.

The wash solvent is typically added to the carotenoid in a ratio of about 1:1 to about 50:1 (v/v) relative to the liquid containing at least one carotenoid used. The wash solvent can be added to the carotenoid in a ratio of about 1:1 to about 40:1; about 1:1 to about 30:1; about 1:1 to about 20:1; about 1:1 to about 15:1; about 1:1 to about 10:1; or about 5:1 to about 10:1 (v/v) relative to the liquid containing at least one carotenoid used.

The bound carotenoid can be contacted with the wash solvent between one and ten times, or until at least a portion or substantially all glycerol esters present with the carotenoid have been removed. In embodiments, the carotenoid is contacted between 5-10 times with the wash solvent. The wash solvent can be monitored for glycerol esters using any analytical method known to those of skill in the art, such as IR spectroscopy, LCMS, GCMS, H-NMR, C-NMR, and the like.

The carotenoids can then be extracted from the washed carotenoid by contact with a suitable organic solvent thereby forming an extract phase containing at least one carotenoid and regenerating the support comprising at least one pi-bond-philic species. The regenerated support comprising at least one pi-bond-philic, species can be then reused in subsequent carotenoid recovery processes. The process further comprises a step of removing the wash solvent prior to the step of contacting the washed carotenoid with said organic solvent.

Any organic solvent that is capable of removing the bound carotenoids from the washed carotenoid can be used. In certain instances, the organic solvent is a competitive binder to the support comprising the silver or pi-bond-philic species. In embodiments, organic solvents such as one or more olefins and/or other ligands that are capable of binding to silver species are used to displace the bound carotenoid from the silver-doped support. The competitive binder can have a higher affinity to the silver species, substantially the same affinity, or a lower affinity relative to the bound carotenoids. Suitable organic solvents include alkanes, unsaturated hydrocarbons (e.g., alkenes and alkynes), alcohols, esters, ethers, thioethers, and combinations thereof. In certain instances, the organic solvent is a food grade solvent.

Suitable unsaturated hydrocarbons can include one or more alkenes, alkynes, and combinations thereof. The site of unsaturation on the hydrocarbon can be at a terminal position of the hydrocarbon, e.g., an α-olefin or terminal alkyne, at an internal position, e.g., vicinal or geminal olefins, and combinations thereof. The alkene can be mono-, di-, tri-, or tetra-substituted.

Unsaturated hydrocarbons include, but are not limited to C4-C30 unsaturated hydrocarbons, C4-C20 unsaturated hydrocarbons, C6-C16 unsaturated hydrocarbons, and combinations thereof. Exemplary unsaturated hydrocarbons include, but are not limited to 1-pentene, 1-hexene, 1,5-dihexene, 1-heptene, 1-octene, 1-nonene, 1-decene, 1-undecene, 1-dodecene, 1-tetradecene, 1-hexadecene, limonene, geraniol, sorbic acid, isoperene, α-piene, myrcene, farnesene, farnesol, citral, caryophylene, zingiberen and combinations thereof.

The organic solvent is typically added to the washed carotenoid in a ratio of about 1:0.5 to about 1:100 (v/v) (liquid containing at least one carotenoid: organic solvent). The organic solvent can be added in a ratio of about 1:1 to about 1:75; about 1:1 to about 1:50; about 1:1 to about 1:25; about 1:1 to about 1:10; about 1:1 to about 1:5; about 1:1 to about 1:3; or about 1:1 to about 1:2 (v/v) (liquid containing at least one carotenoid: organic solvent).

The washed carotenoid can be contacted with the organic solvent between one and ten times, or until at least a portion or substantially all carotenoids bound to the support doped with silver or at least one pi-bond-philic species are dissociated. In the examples, the carotenoid is contacted between 1-3 times with the organic solvent. The organic solvent can be monitored for carotenoids using any analytical method known to those of skill in the art, such as IR spectroscopy, LCMS, GCMS, H-NMR, C-NMR, and the like.

The organic solvent can optionally be separated from the extract phase containing at least one carotenoid thereby forming a carotenoid concentrate. Any method known to those of skill in the art can be used to separate the organic solvent from the extract phase, such as evaporation of the organic solvent (under atmospheric or reduced pressure) or crystallization and/or filtration of the carotenoids present in the extract phase.

After removal of the organic solvent from the extract phase, the remaining carotenoid can have a purity of between about 10% to about 100%, about 20% to about 100%, 30% to about 100%, 40% to about 100%, 50% to about 100%, 60% to about 100%, 70% to about 100%, 70% to about 95%, 70% to about 90%, or about 80% to about 90% (w/w).

The claimed process can be used to recover from about 10% to about 99% of the carotenoids in a liquid containing at least one carotenoid. The claimed process can be used to isolate about 10% to about 90%, about 10% to about 85%, about 10% to about 80%, about 10% to about 75%, about 10% to about 70%, about 20% to about 70%, about 30% to about 70%, or about 50% to about 70% of the carotenoids present in a liquid containing at least one carotenoid.

In embodiments, the process herein comprises the steps of:
a. contacting palm oil with $Ag_2O$, $Ag^+$ intercalated clay, or Ag-silicates thereby forming a mixture comprising a carotene complex and the palm oil;
b. removing the palm oil;
c. contacting the carotene complex with a food grade wash solvent thereby forming a washed carotene complex;
d. removing the food grade wash solvent;
e. extracting the carotene from the carotene complex with a food grade organic solvent to form an extract phase containing the carotene; and
f. removing the food grade organic solvent from the carotene by evaporation.

Exemplary embodiments of a material for reversibly binding to a carotenoid will now be disclosed.

The material can further comprise a support selected from the group consisting of a clay, a zeolite, a cation exchange resin, silica, alumina, activated carbon, or a metal chelating polymer.

In one embodiment, the support has a substantially uniform chemical composition. For instance, the support may be a synthetic clay that is substantially free of transition metals and which is coupled to silver ions. In one embodiment, it is preferred that the silver ions are monovalent, divalent or trivalent.

Under the same reaction conditions, it has advantageously been found that silver-doped synthetic clay would more readily bind to and dissociate from the carotenoid relative to natural clay that contains transition metals other than silver. More advantageously, because transition metals are absent from the support, the dissociation of the carotenoid can be undertaken at less extreme reaction conditions (i.e. at temperatures where the structure of the carotenoid is not compromised or significantly degraded). For example, if the carotenoid is β-carotene, the double bonds of the β-carotene are advantageously more readily retained during dissociation relative to a carotene bound to a support that also contained transition metals other than silver.

In one embodiment, substantially all of the carotenoid is capable of being dissociated from the support in an organic solvent. Advantageously, it is possible to re-use the support in subsequent carotenoid recovery processes.

In instances where the support further comprises a clay, the clay can be a naturally occurring clay, i.e., isolated from nature, or a synthetic clay.

Clays represent a large group of minerals characterized by the presence of aluminum phyllosilicates and can also include other elements, such as iron, magnesium, alkali metals, alkaline earths, and other cations.

Suitable clays can include minerals from the kaolin group, such as kaolinite, dickite, halloysite, and nacrite, the smectite group, such as montmorillonite, and nontronite, the illite group, which includes clay-micas, the chlorite group, and mixed layer clay variations.

Specific examples of clays suitable as supports include, but are not limited to chryolite, chlinochlore, kaolinite, nontronite, paragonite, phlogopite, pyrophyllite, smectite, talc, vermiculite and mixtures thereof. Exemplary smectite clays include bentonite, beidellite, hectorite, montmorillonite, saponite, stevensite, and mixtures thereof.

Synthetic clays can be prepared by reacting a metal salt and a metal silicate in a solvent under suitable conditions to form the desired synthetic clay.

The metal silicate may be any, alkali metal silicate or alkaline earth metal silicate or combination thereof. Exemplary metal silicates include lithium silicate, sodium silicate, potassium silicate, beryllium silicate, magnesium silicate and calcium silicate.

The metal of the metal salt may be a multi-valent metal. This metal may be selected from the group consisting of alkali metals, alkaline earth metals, or a metal of group IIIA, VIIA and VIII of the Periodic Table of Elements. Exemplary metals include sodium, potassium, lithium, magnesium, calcium, aluminum, iron, and manganese.

The anion of the metal salt may be hydroxyl, a halide, such as chloride, bromide, iodide, or fluoride, a carboxylate, such as acetate, or nitrate.

The metal salt and metal silicates may be selected to synthesize the clay particles selected from the group consisting of chryolite, chlinochlore, kaolinite, nontronite, paragonite, phlogopite, pyrophyllite, smectite, talc, vermiculite and mixtures thereof. Exemplary smectite clays include bentonite, beidellite, hectorite, montmorillonite, saponite, stevensite, and mixtures thereof.

In the examples below, the synthetic clay is prepared from $MgCl_2 \cdot 6H_2O$, LiCl, $Na_2Si_3O_7$, and $Na_2CO_3$ in water.

The reactant solution mixture can comprise a molar excess of the metal silicate relative to the metal salt.

Traditional methods for preparing synthetic clays typically employ heating the reaction mixture. However, heating using a radiation source allows heating of a material at substantially the same rate throughout its volume, that is, it enables volumetric heating. Heat energy from the radiation source is transferred through the heated material electromagnetically. Consequently, the rate of heating is not limited by the rate of heat transfer through a material as during conventional or conductive heating, and the uniformity of heat distribution is greatly improved. Heating times may be reduced to less than one percent of that required using conventional or conductive heating.

Exemplary radiation sources include radio waves, microwaves, and infrared. In one embodiment, the radiation source is a microwave radiation source. The two main mechanisms of microwave heating are dipolar polarization and conduction mechanism. Dipolar polarization is a process by which heat is generated in polar molecules. When an electromagnetic field is applied, the oscillating nature of the electromagnetic field results in the movement of the polar molecules as they try to align in phase with the field. However, the inter-molecular forces experienced by the polar molecules effectively prevent such alignment, resulting in the random movement of the polar molecules and generating heat. Conduction mechanisms result in the generation of heat due to resistance to an electric current. The oscillating nature of the electromagnetic field causes oscillation of the electrons or ions in a conductor such that an electric current is generated. The internal resistance faced by the electric current results in the generation of heat. Accordingly, the microwaves may be used to produce high temperatures uniformly inside a material as compared to conventional heating means which may result in heating only the external surfaces of a material.

The microwaves may be applied at a power in the range selected from the group consisting of about 30 W to about 180 KW, about 30 W to about 150 KW, about 30 W to about 120 KW, about 30 W to about 100 KW, about 30 W to about 50 KW, about 30 W to about 25 KW, about 30 W to about 15 KW, about 30 W to about 10 KW, about 30 W to about 5 KW, about 30 W to about 2 KW, about 30 W to about 1200 W, about 50 W to about 1200 W, about 100 W to about 1200 W, about 200 W to about 1200 W, about 300 W to about 1200 W, about 400 W to about 1200 W, about 500 W to about 1200 W, about 600 W to about 1200 W, about 700 W to about 1200 W, about 800 W to about 1200 W, about 900 W to about 1200 W, about 1000 W to about 1200 W, about 30 W to about 1100 W, about 30 W to about 100 W, about 30 W to about 80 W, about 30 W to about 60 W, about 30 W to about 40 W, about 40 W to about 120 W, about 60 W to about 120 W, about 80 W to about 120 W, about 100 W to about 120 W, about 70 W to about 100 W and about 50 W to about 70 W.

Typical frequencies of microwaves may be in the range of about 300 MHz to about 300 GHz. This range may be divided into the ultra-high frequency range of 0.3 to 3 GHz, the super high frequency range of 3 to 30 GHz and the extremely high frequency range of 30 to 300 GHz. Common sources of microwaves are microwave ovens that emit microwave radiation at a frequency of about 0.915, 2.45, or 5.8 GHz. The microwaves may be applied with a frequency in the range selected from the group consisting of about 0.3 GHz to about 300 GHz, about 0.3 GHz to about 200 GHz, about 0.3 GHz to about 100 GHz, about 0.3 GHz to about 50 GHz, about 0.3 GHz to about 10 GHz, about 0.3 GHz to about 5.8 GHz, about 0.3 GHz to about 2.45 GHz, about 0.3 GHz to about 0.915 GHz and about 0.3 GHz to about 0.9 GHz.

The process for preparing the synthetic clay may further comprise a step for removing the clay particles from the reactant solution mixture. The removed clay particles may then be dried to substantially remove extraneous water therefrom. The drying can be carried out at a temperature of about 250° C. for about 8 hours.

The particle size of the clay particles may be in the nanometer range to the micrometer range. In one embodiment, the mean size of the clay particles ranges from about 20 nm to 120 nm.

Zeolites are microporous aluminosilicate minerals, which can be characterized by their porous structures that can accommodate a wide variety of cations, such as sodium, potassium, calcium, magnesium, and many others. These cations can be readily exchanged for other cations in solution.

Zeolites useful as supports include, but are not limited to edingtonite, gonnardite, kalborsite, mesolite, natrolite, paranatrolite, scolecite, thomsonite, analcime, leucite, pollucite, wairakite, laumontite, yugawaralite, goosecreekite, montesommaite, amicite, boggsite, garronite, gismondine, gobbinsite, harmotome, phillipsite, merlinoite, mazzite, paulingite, perlialite, bellbergite, bikitaite, erionite, faujasite, ferrierite, gmelinite, offretite, willhendersonite, chabazite, levyne, maricopaite, mordenite, dachiardite, epistilbite, barrerite, brewsterite, clinoptilolite, heulandite, stilbite, cowlesite, herschelite, pentasil (also known as ZSM-5), sodium dachiardite, stellerite, tetranatrolite, tschernichite, wellsite, and combinations thereof.

Cation exchange resins are typically polymers containing one or more pendant anionic groups together with a cation that can be exchanged when brought into contact with the appropriate cation in solution. The polymer may be synthetic (e.g., polymers or copolymers of acrylic acid, methacrylic acid, sulfonated styrene, sulfonated divinylbenzene), or partially synthetic (e.g., modified cellulose and dextrans). The covalently bound anionic groups may be strongly acidic (e.g., sulfonic or sulfate acid groups) or weakly acidic (e.g., carboxylic acid). Other types of charged groups can also be used, including any organic group that bears an acidic, for example, a carboxylic, phosphoric, phenolic, sulfuric, sulfonic or other acidic group.

Suitable resins include, but are not limited to, "Dowex" resins and others made by Dow Chemical; "Amberlite", "Amberlyst" and other resins made by Rohm and Haas; "Indion" resins made by Ion Exchange, Ltd. (India), "Diaion" resins by Mitsubishi; Type AG and other resins by BioRad; "Sephadex" and "Sepharose" made by Amersham; resins by Lewatit, sold by Fluka; "Toyopearl" resins by Toyo Soda; "IONAC" and "Whatman" resins, sold by VWR; and "BakerBond" resins sold by J T Baker. Particular resins known to be useful include Amberlite IRP-69 (Rohm and Haas), and INDION 224, INDION 244, and INDION 254 (Ion Exchange (India) Ltd.). These resins are sulfonated polymers composed of polystyrene cross-linked with divinylbenzene.

Suitable metal ion chelating polymers include those with a polymeric backbone, such polystyrene, polyacrylate, and polymethacrylate, which include pendant groups that are capable of binding a metal and/or metal ion. Such pendant groups include neutral and ionic ligands. Suitable ligands include, but are not limited to phosphines, phosphates, phosphinates, amines (e.g., aliphatic, aromatic, and heteroaromatic), imines, amides, ethers, thio ethers, alcohols, thiols, and the like.

The disclosed material comprising at least one pi-bond-philic species and a support can be present together in admixture, intercalated, complexed, adsorbed, absorbed, as an ion pair, and combinations thereof.

In instances, where the pi-bond-philic species and the clay are intercalated, they can be prepared by dissolving the clay and the pi-bond-philic species in a solvent, typically water, and stirring under conditions which promote intercalation. The intercalated pi-bond-philic species is prepared from a starting inorganic clay by exchanging at least some or substantially all of the exchangable inorganic cations thereof for the pi-bond-philic species (i.e., replacing at least some of the native inorganic cations, e.g., $Li^+$, $Na^+$, $Ca^{2+}$, and/or $H^+$ with pi-bond-philic cations). The cation exchanging capacity of the starting inorganic clay can be about 0.001 to about 100 mol % with the pi-bond-philic cations. In certain embodiments, the cation exchanging capacity is about 5 to about 100 mol %, about 10 to about 100 mol %, about 20 to about 100 mol %, about 30 to about 100 mol %, about 30 to about 90 mol %, about 30 to about 80 mol %, about 30 to about 70 mol %, about 30 to about 60 mol % with the pi-bond-philic cations. Where the cation exchange capacity of the starting inorganic clay is less than 100 mol % exchanged with the pi-bond-philic cations, the remainder of the cation exchanging capacity can be unexchanged native inorganic cations.

In one embodiment, the disclosed support is capable of exchanging at least partially or completely its indigenous cations with silver ions. In embodiments, the cation exchanging capacity of the disclosed support is about 5 to about 100 mol %, about 10 to about 100 mol %, about 20 to about 100 mol %, about 30 to about 100 mol %, about 30 to about 90 mol %, about 30 to about 80 mol %, about 30 to about 70 mol %, about 30 to about 60 mol % with silver ions.

The intercalated clay pi-bond-philic species can have the formula $Na_{1.2-(X\cdot Y)}(M^{(Y)})_X[Mg_{4.8}Li_{1.2}Si_8O_{20}(OH)_4]$, wherein X is a number selected from 0.01-1.2; Y is a whole number selected from 1-4; M is Ag, Au, Ca, Cd, Cu, Fe, Hg, Ir, Ni, Pd, Pt, Rh, Zn, and combinations thereof; and wherein the clay has a net neutral charge. In one embodiment, it is preferred that the disclosed material has the formula $Na_{1.2-(X\cdot Y)}(Ag^{(Y)})_X[Mg_{4.8}Li_{1.2}Si_8O_{20}(OH)_4]$, wherein X is a number selected from 0.01-1.2; Y is a whole number, selected from 1-3; and wherein the material has a net neutral charge. In embodiments, X may be selected from the group consisting of: 0.01, 0.02, 0.04, 0.05, 0.1, 0.15, 0.2, 0.3, 0.4, 0.6, 0.8, 1.0, 1.1 and 1.2. In one embodiment, it is preferred that the multiple of X and Y is a number selected from the group consisting of: 0.1, 0.2, 0.3, 0.4, 0.5, 0.6, 0.7, 0.8, 0.9, 1.0 and 1.2.

Y represents the oxidation state of the metal M. Y can be +1, +2, +3, +4, +5, +6, +7, +8, and combinations thereof. The net charge of the formula above can be zero, i.e., the material is charge balanced.

X can be any number between 0.01 to 0.6, such as 0.05, 0.1, 0.15, 0.20, 0.25, 0.30, 0.35, 0.40, 0.45, 0.50, 0.55, and 0.60. In certain instances, X can be 0.05-0.6, 0.05-0.5, 0.05-0.4, 0.05-0.3, 0.05-0.2, 0.05-0.15, 0.05-0.1, 0.2-0.4, 0.1-0.3, or 0.1-0.2.

M can be Ag, Au, Ca, Cu, Fe, Zn, and combinations thereof.

In certain embodiments, the intercalated clay pi-bond-philic species can have the formula $Na_{1.2-(X\cdot Y)}(M^{(Y)})_X[Mg_{4.8}Li_{1.2}Si_8O_{20}(OH)_4]$, wherein x is a number selected from 0.01-0.6 for divalent pi-bond-philic species, i.e., Y is +2, X is a number selected from 0.01-0.4 for trivalent pi-bond-philic species, i.e., metal Y is +3, and X is a number selected from 0.01-0.3 for tetravalent pi-bond-philic species, i.e., Y is +4.

Monovalent pi-bond-philic species can include, but are not limited to $Ag^+$, $Cu^+$, $Au^+$, $Hg^+$, and $Cd^+$.

Divalent pi-bond-philic species can include, but are not limited to $Ag^{2+}$, $Zn^{2+}$, $Ca^{2+}$, $Ni^{2+}$, $Cu^{2+}$, $Au^{2+}$, $Pd^{2+}$, $Pt^{2+}$, $Fe^{2+}$, $Rh^{2+}$, $Ir^{2+}$, $Hg^{2+}$, and $Cd^{2+}$.

Trivalent pi-bond-philic species can include, but are not limited to $Au^{3+}$, $Fe^{3+}$, $Rh^{3+}$, and $Ir^{3+}$.

Tetravalent pi-bond-philic species can include, but are not limited to $Ni^{4+}$, $Pd^{4+}$, $Pt^{4+}$, and $Ir^{4+}$.

In certain embodiments, the clay has the formula $Na_{1.2-x}Ag_x[Mg_{4.8}Li_{1.2}Si_8O_{20}(OH)_4]$, wherein x is a number selected from 0.1-1.2. In the examples below, the intercalated clay pi-bond-philic, species is $Ag_{1.2}[Mg_{4.8}Li_{1.2}Si_8O_{20}(OH)_4]$.

In certain instances, the pi-bond-philic species can be used in the absence of a support. In such instances, the pi-bond-philic species is contacted with the liquid containing at least one carotenoid directly. Suitable pi-bond-philic species include, but are not limited to chloride, bromide, iodide, fluoride, acetate, oxide, hydroxide, nitrate, and acetate salts of Ag, Zn, Ca, Ni, Cu, Au, Pd, Pt, Fe, Ni, Rh, Ir, Hg, and Cd. The metals can be in the +1, +2, +3, or +4 oxidation state. Exemplary salts include silver silicates ($Ag_4SiO_4$, $Ag_2SiO_3$), $Ag_2O$, AgO, AgOAc, and $Ag(OAc)_2$.

The support comprising at least one pi-bond-philic species can be used directly or disposed onto a carrier, a filtration device, or a cartridge.

The amount of the support comprising at least one pi-bond-philic species added to the liquid containing at least one carotenoid can depend on the amount and type of the carotenoid present in the liquid, the nature of the liquid, the type of pi-bond-philic species being used, and the contact conditions, e.g., the length of time the support will remain in contact with the liquid, and the temperature at which the material and the liquid are contacted.

The liquid containing at least one carotenoid is allowed to remain in contact with the support comprising at least one pi-bond-philic species for an amount of time sufficient to allow at least some of the carotenoids present in the liquid to bind to the support, thereby forming a carotenoid complex.

The reversible binding of the carotenoid can form as a result of complexation, adsorption, absorption, and combinations thereof to the pi-bond-philic species and/or the support. In instances where more than one type of carotenoid is present in the liquid (e.g., both α-carotene and β-carotene), the carotenoid can comprise more than one type of carotenoid present in the liquid bound to the pi-bond-philic species. In a preferred embodiment, the carotenoid is α-carotene, β-carotene, and combinations thereof.

BRIEF DESCRIPTION OF DRAWINGS

The accompanying drawings illustrate disclosed embodiments and serves to explain the principles of the disclosed embodiments. It is to be understood, however, that the drawings are designed for purposes of illustration only, and not as a definition of the limits of the invention.

EXAMPLES

Non-limiting examples of the present disclosure will be further described, which should not be construed as in any way limiting the scope of the disclosure.

Example 1

Preparation of a Synthetic Clay

To synthesize the clay, $MgCl_2.6H_2O$ (104 g), LiCl (1.3 g), $Na_2Si_3O_7$ (166 g) and $Na_2CO_3$ (29.5 g) were dissolved in $H_2O$ (1800 ml). After stirring it for 30 minutes, the solution mixture was treated in a domestic microwave oven (2400 W, 60 minutes) The reaction product was filtered, washed with water (2500 ml) and was dried at 110° C. (16 hours) to yield 60 g of the desired synthetic clay.

X-ray diffraction analysis of the synthetic clay indicates that it is a hectorite clay (Monoclinic, space group C 2/m) with a interlayer spacing of ~16 Å). X-ray fluorescence analysis of the prepared synthetic clay indicates the clay consists of $Na_2O$ (1.91%), MgO (17.76%), $SiO_2$ (47.37%) by wt % and $H_2O$.

Example 2

Preparation of a Silver Intercalated Synthetic Clay

To the synthetic clay (5 g) prepared in example 1 dispersed in $H_2O$ (500 ml), a solution of $AgNO_3$ salt (1 g) was added followed by stirring for 24 hours. Then the Ag-intercalated clay was filtered and washed with deionized $H_2O$ followed by drying at 80° C. (16 hours). The dried Ag-Clay was used for carotenoid separation.

Figure 1:
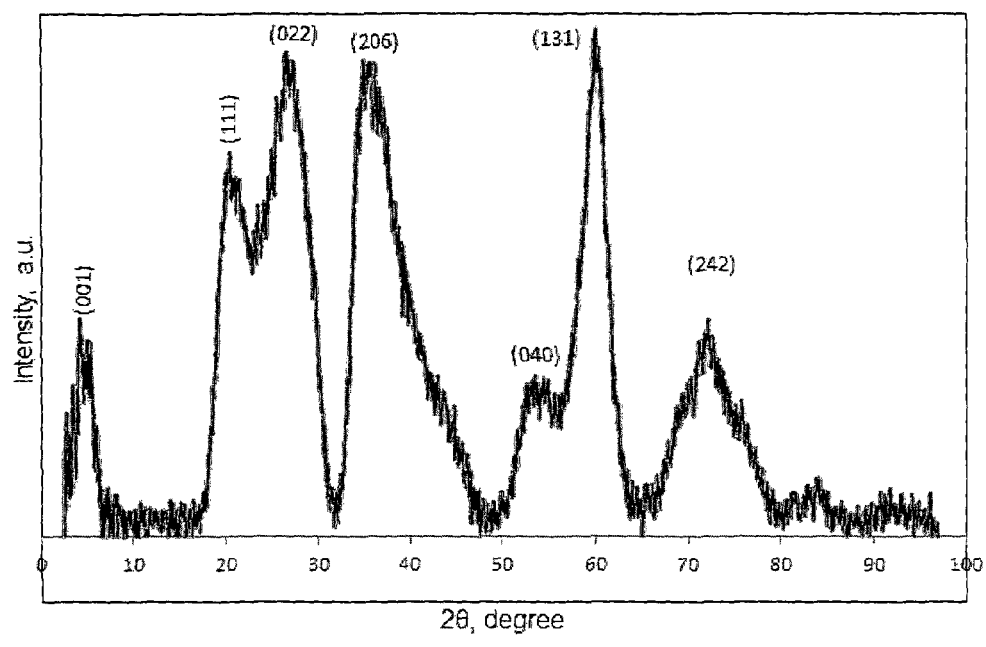
FIG. 1 depicts X-ray diffraction analysis of a silver intercalated clay sample.

X-ray diffraction analysis of the synthetic clay indicates that the structure of the Ag intercalated synthetic clay is $Ag_{1.2}[Mg_{4.8}Li_{1.2}Si_8O_{20}(OH)_4]$ (FIG. 1). X-ray fluorescence analysis indicates that the silver intercalated clay consists of Ag (30-52 wt %) with MgO (5.02-12.28 wt %), $SiO_2$ (16.64-30.37 wt %) and $H_2O$ (Table. 1).

TABLE 1

X-ray fluorescence analysis of the silver intercalated clay

| Sample | Compound | w/w (%) |
|---|---|---|
| Sample 1 | MgO | 5.02 |
| | $SiO_2$ | 16.64 |
| | Ag | 52.43 |
| | Loose Water | 6.96 |
| | Bounded Water | 8.24 |
| | OH + Volatile Organic | 10.54 |
| | $CO_2$ | 0.16 |
| | Total | 100.00 |
| Sample 2 | MgO | 12.28 |
| | $SiO_2$ | 30.37 |
| | CaO | 0.13 |
| | Cl | 1.17 |
| | Ag | 32.67 |
| | Loose Water | 5.42 |
| | Bounded Water | 7.94 |
| | OH + Volatile Organic | 7.07 |
| | $CO_2$ | 2.97 |
| | Total | 100.00 |

Example 3

Preparation of Ag_o

To a silver nitrate (2 g) solution (water, 50 ml) an aqueous solution of NaOH (0.7 g in 5 ml water) was added with constant stirring at room temperature for 15 minutes. The precipitate was dried at 80° C. for 2 hours and characterized by XRD and BET surface area (Yield 1.2 g).

Figure 2:
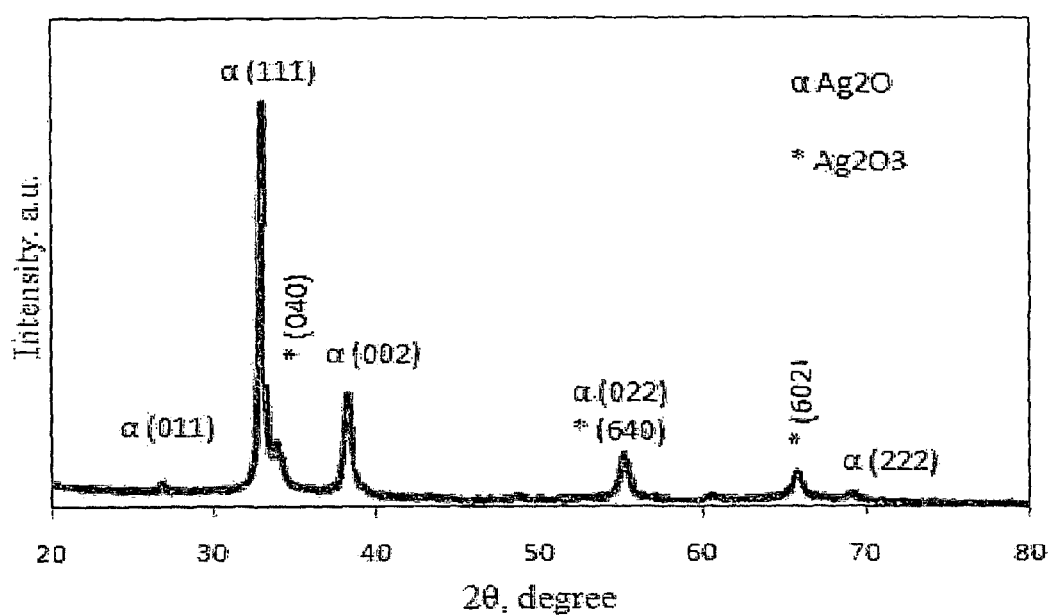
FIG. 2 depicts X-ray diffraction analysis silver(I)oxide sample.

X-ray diffraction analysis indicated that the formed material was $Ag_2O$ with a small amount of Ag_o (FIG. 2).

Example 4

Preparation of Silver Silicate

Figure 3:
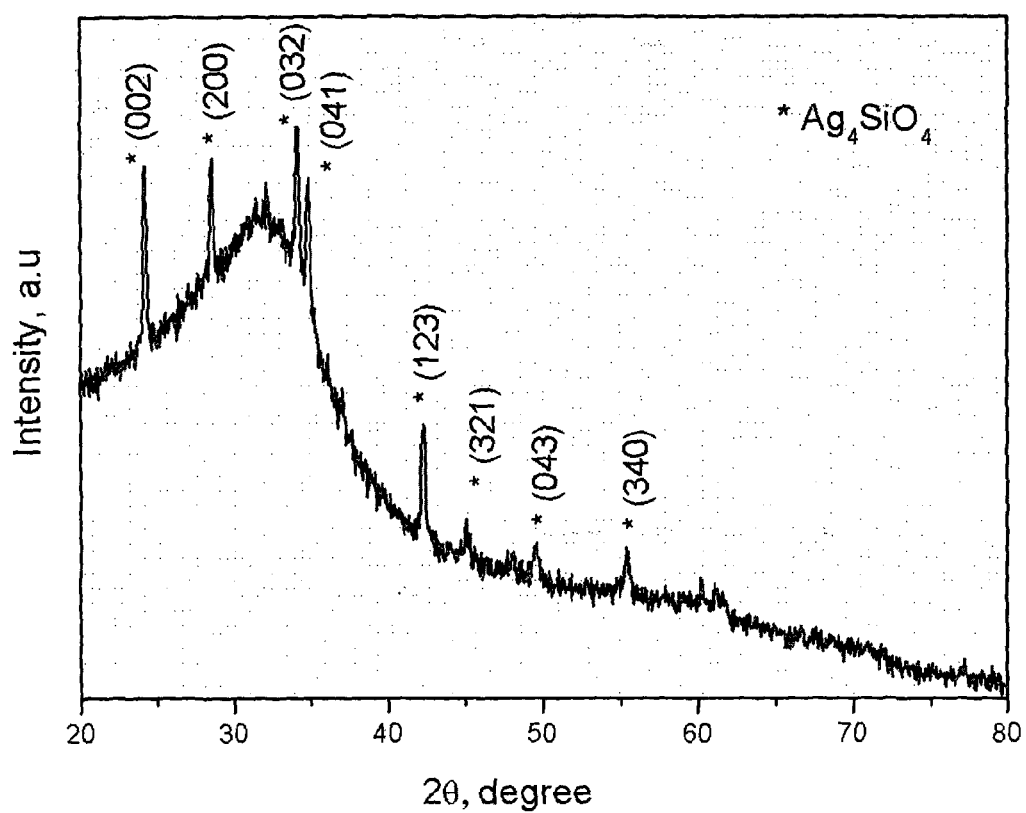
FIG. 3 depicts X-ray diffraction analysis of a silver silicate sample.

To a silver nitrate (1 g) solution (water, 30 ml) an aqueous solution of $Na_2Si_3O_7$ (33 wt %) was added with constant stirring at room temperature for 10 minutes. Acetone (20 ml) was added to accelerate the precipitation of the desired product. The precipitate was washed with water (100 ml) followed by acetone (50 ml) and dried at 50° C. X-ray diffraction analysis shows that the formed material was $Ag_2SiO_4$ with some amorphous phases (FIG. 3).

Example 5

Isolation of Carotenoids From Palm Oil

For carotene extraction, Ag-clay (0.5 g) was added to crude palm oil (10 g) with constant stirring. The optimum stirring was found to be 2 hours. The oil was separated from the carotenes absorbed clay by centrifugation followed by washing with an organic solvent (5×10 ml), the solvent could be preferably acetone, hexane. The washing was performed till the adsorbed oil came out and was identified by IR the glycerides C=O peaks.

Figure 4:
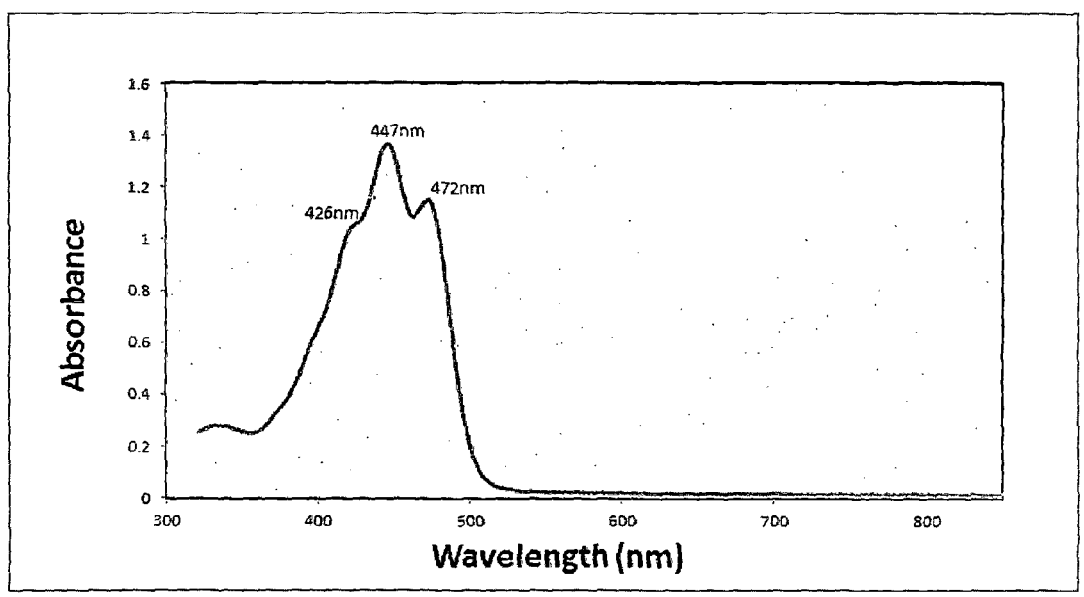
FIG. 4 depicts the UV-visible absorption spectrum of carotenoids separated from crude palm oil.
Figure 5:
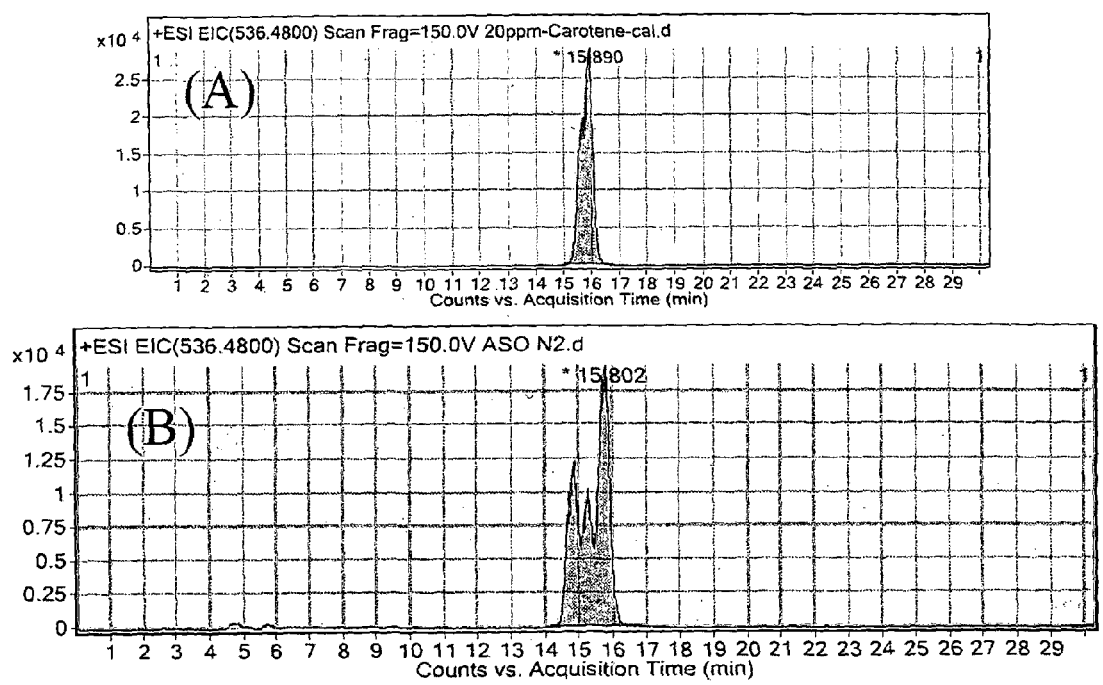
FIG. 5 depicts the liquid chromatogram of (A) standard carotene (B) carotenoids separated from crude palm oil.

Octadecene or 1,5-Hexadiene (5 ml) was then added to the washed carotenoid complex and allowed to mix. The hexadecane was then collected by filtering off the solids. The alkenes were then removed under reduced pressure to yield the isolated carotenoids. The separation was confirmed by UV-visible spectroscopy (FIG. 4) and liquid chromatography (FIG. 5). As shown in FIG. 4, it can be seen that the absorption was observed at 472 nm, 447 nm and 426 nm which are characteristic absorption peaks for carotenoids. In addition, it can be seen from the chromatograms in FIG. 5 that the retention time of the isolated carotenoids which contains carotene, separated from crude palm oil (B), is identical to that of standard carotene (A).

Typical yield of carotenoids was 0.6-2.2 mg, which consisted of ~35% of α-carotene, 54% of β-carotenes, 3% of γ-carotene and lycopene. This represents about a 10-70% recovery of the carotenoids initially present in the crude palm oil. The results of these experiments are tabulated in Table 2.

TABLE 2

Carotenoids separated from crude palm oil

| Absorbent | Wt % of absorbent in CPO* | Carotene absorbed (wt % of the initial concentration) | Extraction solvent | Carotene extracted |
|---|---|---|---|---|
| Ag-Clay | 2 | 8.2 | Octadecene | 0.1-0.5 mg/l |
| Ag-Clay | 2 | 8.2 | 1,5 Hexadiene | 0.8 mg/l |
| Ag-Clay | 5 | 11 | 1,5 Hexadiene | 1.2 mg/l |
| Ag-Clay | 10 | 14.2 | 1,5 Hexadiene + soya oil | 6 mg/l(after hexadiene is removed) |
| AgO | 2 | 16.8 | 1,5 Hexadiene | 1.87 mg/l |
| AgO | 2 | 16.8 | 1,5 Hexadiene + soya oil | 4 mg/l(after hexadiene is removed) |
| Ag-silicates | 5 | 10 | 1,5 Hexadiene + soya oil | 1.5 mg/l(after hexadiene is removed) |

*CPO = crude palm oil.

Example 6

The Effect of Temperature on the Isolation of Carotenoids from Palm Oil

In another set of experiments, carotenoids were isolated from crude palm oil as described in Example 5, but the crude palm oil and clay mixture was heated at 40° C. The carotene separation amount was higher (0.6-4.2 mg) compared to the room temperature process.

Example 7

Isolation of Carotenoids from Palm Oil Using AgO

In another set of experiments, Ag$_2$O (0.2 g) was used instead of Ag-clay in the treatment of crude palm oil (10 g). The process was the same as described in Example 5 as discussed above. Using Ag$_2$O, 0.6-1.8 mg of carotenoids were extracted from 10 g of crude palm oil.

Example 8

Isolation of Carotenoids from Palm Oil Using Ag-silicates

In another set of experiments, Ag-silicates (0.2 g) was used instead of Ag-clay in the treatment of crude palm oil (6 g). The process was the same as described in Example 5 as discussed above. Using Ag-silicates, 0.5-1.5 mg of carotenoids was extracted from 10 g of crude palm oil.

Example 9

Effect of Crude Palm Oil Concentration on Carotene Recovery from Palm Oil

In another set of experiments, the effect of concentration of the palm oil on carotenoid recovery was studied. Dilution of the crude palm oil with acetone and hexane (2 g of crude palm oil diluted in 15 ml of acetone or hexane) resulted in an increased carotenoid absorption when 0.5 g of Ag-clay was used. Hexane as solvent resulted in higher carotene binding compared to acetone solvent. This change resulted in an increase in carotenoids isolated in the concentrated extract phase from 45 ppm to 50 ppm.

The complexed carotenoid from the carotenoid complex was separated by treating with other extraction solvents (hexadecene, 1,5 hexadiene, limonene, geraniol, sorbic acid, isoperene, α-piene, myrcene, farnesene, farnesol, citral, caryophylene, zingiberene, 5 ml). The process involved stirring of the carotenoid complex in the presence of the solvent (15-30 minutes).

The extraction solvents had high binding efficiency with the metal ions and hence replaced the carotene-metal ions bonding; carotene came out to the solvent medium. The extracted carotene was confirmed by IR and UV-spectroscopy.

The above described process typically resulted in about 0.1 mg of isolated carotenoids, which represented a 20-80% recovery of the carotenoids initially present in the crude palm oil. The results of these experiments are tabulated in Table 3.

TABLE 3

Carotenoids separated from crude palm oil

| Absorbent | Wt % of absorbent in CPO | % of Dilution | Heat | % Carotene absorbed (wt % of the initial concentration) |
|---|---|---|---|---|
| Ag-clay | 10 | 0 | RT | 16.7 |
| Ag-clay | 10 | 0 | 40° C. | 60.5 |
| Ag-clay | 20 | 0 | 40° C. | 77.6 |
| Ag-clay | 25 | 20 (acetone) | RT | 21.48 |
| Ag-clay | 25 | 20 (hexane) | RT | 26.7 |
| Ag-clay | 40 | 20 (hexane) | RT | 70.2 |

*CPO = crude palm oil; RT = room temperature.

APPLICATIONS

The material, for reversibly binding to a carotenoid and the carotenoid isolation process described herein can be used in connection with the recovery and/or isolation of carotenoids, such as α-carotene and β-carotene, from a broad range of liquids containing such carotenoids. Exemplary liquids include palm oil, crude palm oil, crude palm olein, red palm oil/olein, palm stearin, neutralized red palm oil, neutralized red palm olein, sunflower oil, coconut oil, wheat germ, carrot oil, soybean, rapeseed, olive and derivative of such oils.

The material and carotenoid isolation process can be used in the recovery and/or isolation of carotenoids from liquid extracts derived from, carotenoid producing fungi, carotenoid producing bacteria, carotenoid producing microalgae, and carotenoid producing yeast.

The material and carotenoid isolation process can also be used in the recovery, isolation, and/or purification of carotenoids prepared by chemical synthesis. Crude carotenoids prepared by chemical synthesis can be diluted in an organic solvent. The resulting solution comprising the carotenoid can be subjected to the process described herein to at least partially purify the carotenoids present therein.

The material and isolation process described herein can also be used in the recovery and/or isolation of other olefinic or poly/olefinic hydrocarbons from natural sources or in connection with the chemical synthesis of such compounds.

The carotenoids provided by the material and, isolation process described herein have a wide range of benefits to human health due to their biological functions. Being an antioxidant, carotenoids are vital, for cell health due to their ability to prevent oxidative damage of the cellular components. Epidemiological evidence supporting a protective effect of carotenoids to the development of chronic and degenerative diseases, such as cancer, has grown considerably.

Due to the nutraceutical properties of the carotenoids described herein, they are also commonly used in the food and biofuel industry. For example, they are used to reinforce fish color, which increases consumers' perception of quality. More importantly, carotenoids have been proposed as added-value compounds that could contribute to make, microalgal biofuel production economically feasible. High oil prices, competing demands between foods and other biofuel sources, and the world food crisis, have ignited interest in microalgae as promising feedstocks for biofuels. The productivity of these photosynthetic microorganisms in converting carbon dioxide into carbon-rich lipids greatly exceeds that of agricultural oleaginous crops, without competing for arable land. Hence, carotenoid-enriched microalgae production is steeply becoming an attractive business.

It will be apparent that various other modifications and adaptations of the invention will be apparent to the person skilled in the art after reading the foregoing disclosure without departing from the spirit and scope of the invention. It is intended that all such modifications and adaptations come within the scope of the appended claims.

The invention claimed is:

1. A material for reversibly binding to a carotenoid, the material comprising:
 a support coupled to silver ions in an amount to enable reversibly binding with said carotenoid, and wherein, with the exception of silver ions, said support is substantially free of transition metals.

2. The material of claim 1, wherein said support has a larger surface area relative to natural clay.

3. The material of claim 1, wherein said support has a total surface area of from 400 m$^2$/g to 700 m$^2$/g.

4. The material of claim 1, wherein the support has a substantially uniform chemical composition.

5. The material of claim 1, wherein said support is synthetic clay.

6. The material of claim 5, wherein said silver ions is monovalent, divalent or trivalent.

7. The material of claim 1, wherein said support is capable of at least partially or completely exchanging its indigenous cations with silver ions.

8. The material of claim 1, having a formula $Na_{1.2-(X \cdot Y)}(Ag^{(Y)})X[Mg_{4.8}Li_{1.2}Si_8O_{20}(OH)_4]$, wherein X is a number selected from 0.01-1.2; Y is a whole number selected from 1-3; and wherein the material has a net neutral charge.

9. The material of claim 8, wherein the multiple of X and Y is 1.2.

10. The material of claim 1, wherein substantially all of the carotenoid is capable of being dissociated from said support in an organic solvent.

11. The material of claim 1, wherein said support is a synthetic hectorite clay, wherein at least 70 mol % to 100 mol % of the sodium ions present in said hectorite clay have been exchanged with silver ions.

12. A process for reversibly binding the material according to claim 1 to a carotenoid, the process comprising the steps of:
 contacting the support with the carotenoid under binding conditions to bind it thereto; and
 dissociating the carotenoid from the support under dissociation conditions to release said carotenoid.

13. The process of claim 12, wherein the support is selected to have a higher surface area relative to natural clay.

14. The process of claim 13, wherein the support is selected to have surface area of from 400 m$^2$/g to 700 m$^2$/g.

15. The process of claim 12, wherein the support is selected to have a substantially uniform chemical material.

16. The process of claim 12, wherein the support is synthetic clay.

17. The process of claim 12, further comprising, prior to said contacting step, a step of at least partially or completely exchanging indigenous cations of said support with silver ions.

18. The process of claim 12, wherein said silver ions or silver of said silver-containing compound is monovalent, divalent or trivalent.

19. The process of claim 12, wherein the support has a formula:
 $Na_{1.2-(X \cdot Y)}(Ag^{(Y)}) \times [Mg_{4.8}Li_{1.2}Si_8O_{20}(OH)_4]$,
 wherein X is a number selected from 0.01-1.2; and
 Y is a whole number selected from 1-3; and
 wherein the material has a net neutral charge.

20. The process of claim 19, wherein the support is selected such that the multiple of X and Y is 1.2.

21. The process of claim 12, further comprising the steps of:
 contacting the carotenoid with a wash solvent to form a washed carotenoid; and
 contacting the washed carotenoid with an organic solvent to form an extract phrase containing carotenoids.

22. The process of claim 12, wherein the support is incorporated into a filtration device.

23. The process of claim 12, wherein the carotenoid is provided in a liquid selected from a fruit oil, vegetable oil, or an extract derived from the group selected from carotenoid producing fungi, carotenoid producing bacteria, carotenoid producing microalgae, and carotenoid producing yeast.

24. The process of claim 23, wherein the liquid is a palm oil.

25. The process of claim 12, wherein the carotenoid is α-carotene, β-carotene, and combinations thereof.

26. The process of claim 23, wherein the support is present in an amount of about 0.01:1 to about 0.1:1 by weight relative to the liquid.

27. The process of claim 12, wherein the time for contacting the carotenoid with the support is from about 10 minutes to about 6 hours.

28. The process of claim 21, further comprising a step of removing the wash solvent prior to the step of contacting the washed carotenoid with said organic solvent.

29. The process of claim 28, wherein the organic solvent is selected from the group consisting of alkanes, alkenes, alkynes, alcohols, ketones, esters, ethers, and combinations thereof.

30. The process of claim 21, wherein the wash solvent and the organic solvent are food grade solvents.

31. The process of claim 21, further comprising a step of removing the organic solvent from the extract phase containing carotenoid by evaporation.

32. The process of claim 12, comprising the steps of:
   a. contacting palm oil with $Ag_2O$, $Ag^+$ intercalated clay, or Ag-silicates thereby forming a mixture comprising a carotene complex and the palm oil;
   b. removing the palm oil;
   c. contacting the carotene complex with a food grade wash solvent thereby forming a washed carotene complex;
   d. removing the food grade wash solvent;
   e. extracting the carotene from the carotene complex with a food grade organic solvent to form an extract phase containing the carotene; and
   f. removing the food grade organic solvent from the carotene by evaporation.

* * * * *

UNITED STATES PATENT AND TRADEMARK OFFICE
CERTIFICATE OF CORRECTION

| | | |
|---|---|---|
| PATENT NO. | : 9,592,499 B2 | |
| APPLICATION NO. | : 14/398835 | |
| DATED | : March 14, 2017 | |
| INVENTOR(S) | : Pretap Kumar Deheri, Varadalambedu Srinivasan Nithianandam and Mahesh Dahyabhai Patel | |

It is certified that error appears in the above-identified patent and that said Letters Patent is hereby corrected as shown below:

For the inventor listed as Srinivasan Varadalambedu Nithianandam, the correct listing of this inventor's name is "Varadalambedu Srinivasan Nithianandam".

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*